US00PP19148P2

(12) United States Plant Patent
Meilland

(10) Patent No.: US PP19,148 P2
(45) Date of Patent: Aug. 26, 2008

(54) SHRUB ROSE PLANT NAMED 'MEIDRIFORA'

(50) Latin Name: *Rosa hybrida*
Varietal Denomination: cv. Meidrifora

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/802,404

(22) Filed: May 22, 2007

(51) Int. Cl.
*A01H 5/00* (2006.01)

(52) U.S. Cl. ..... Plt./108

(58) Field of Classification Search ..... Plt./108
See application file for complete search history.

*Primary Examiner*—Annette H Para
*Assistant Examiner*—S. B. McCormick-Ewoldt
(74) *Attorney, Agent, or Firm*—Buchanan Ingersoll & Rooney PC

(57) ABSTRACT

A new and distinct variety of shrub rose plant is provided which forms in abundance on a nearly continuous basis attractive double cup-like deep-coral-orange blossoms that self clean well. A spreading ground cover growth habit is displayed. The plant forms glossy medium-green foliage that contrasts nicely with the blossom coloration. The plant develops well following asexual propagation. The resistance to Black Spot, Powdery Mildew, and Rust is excellent. The new variety is particularly well suited for providing ornamentation in small areas. It performs well as a mass planting and when grown in containers.

2 Drawing Sheets

Botanical/commercial classification: *Rosa hybrida*/Shrub Rose Plant.
Varietal denomination: cv. Meidrifora.

SUMMARY OF THE INVENTION

The new variety of *Rosa hybrida* shrub rose plant of the present invention was created by artificial pollination wherein two parents were crossed which previously had been studied in the hope that they would contribute the desired characteristics. The female parent (i.e., the seed parent) was 'The Fairy' variety (non-patented in the United States). Such female parent was formed by the cross of the 'Paul Crampel' variety (non-patented in the United States) and the 'Lady Gay' variety (non-patented in the United States). The male parent (i.e., the pollen parent) of the new variety was the product of the cross of the 'Kormax' variety (non-patented in the United States) and an unnamed seedling (non-patented in the United States). The parentage of the new variety can be summarized as follows:

'The Fairy'×('Kormax'×Unnamed Seedling).

The seeds resulting from the above pollination were sown and small plants were obtained which were physically and biologically different from each other. Selective study resulted in the identification of a single plant of the new variety.

It was found that the new Shrub Rose plant of the present invention possesses the following combination of characteristics:

(a) abundantly forms in clusters on a nearly continuous basis attractive double cup-like deep-coral-orange blossoms that self clean well, (b) exhibits a spreading ground cover growth habit, (c) forms glossy medium-green foliage that contrasts well with the blossom coloration, (d) develops well following asexual reproduction, (e) is highly resistant to Black Spot, Powdery Mildew, and Rust; and (f) is particularly well suited for providing attractive ornamentation as a mass planting and when grown in containers.

The new variety well meets the needs of the horticultural industry. It can be grown to advantage as ornamentation in parks, gardens, public areas, and in residential settings where attractive ornamentation is desired. It is particularly well suited for growing in small areas as a ground cover, in a mass planting, and in containers.

The new variety of the present invention also can be readily distinguished from its ancestors and other rose varieties. For instance, 'The Fairy' female parent forms dissimilarly colored light-pink blossoms and displays a taller growth habit. The 'Kormax' variety ancestor forms dissimilar medium-red single blossoms. The 'Meipadan' variety (U.S. Plant Pat. No. 15,487) displays a similar growth habit and forms white single blossoms. The 'Meidarin' variety (U.S. Plant Pat. No. 13,291) also displays a similar growth habit, combined with less hardiness, and the formation of vibrant orange blossoms.

The characteristics of the new variety have been found at Waso, Calif., U.S.A., and near West Grove, Pa., U.S.A., to be homogeneous and stable and to be strictly transmissible by asexual propagation, such as budding, grafting, and the rooting of cuttings from one generation to another. The new variety reproduces true to type by such asexual propagation. Good plant development has been observed regardless of the mode of asexual propagation.

The new variety has been named 'Meidrifora', and is being marketed under the CORAL DRIFT trademark.

BRIEF DESCRIPTION OF THE PHOTOGRAPHS

The accompanying photographs show, as nearly true as it is reasonably possible to make the same in a color illustrations of this character, a typical flowering plant of the new variety. The illustrated rose plant of the new variety was approximately three years of age and was observed during June, 2006 while growing outdoors on 'Dr. Huey' rootstock near West Grove, Pa., U.S.A.

DETAILED DESCRIPTION

Figure 1:
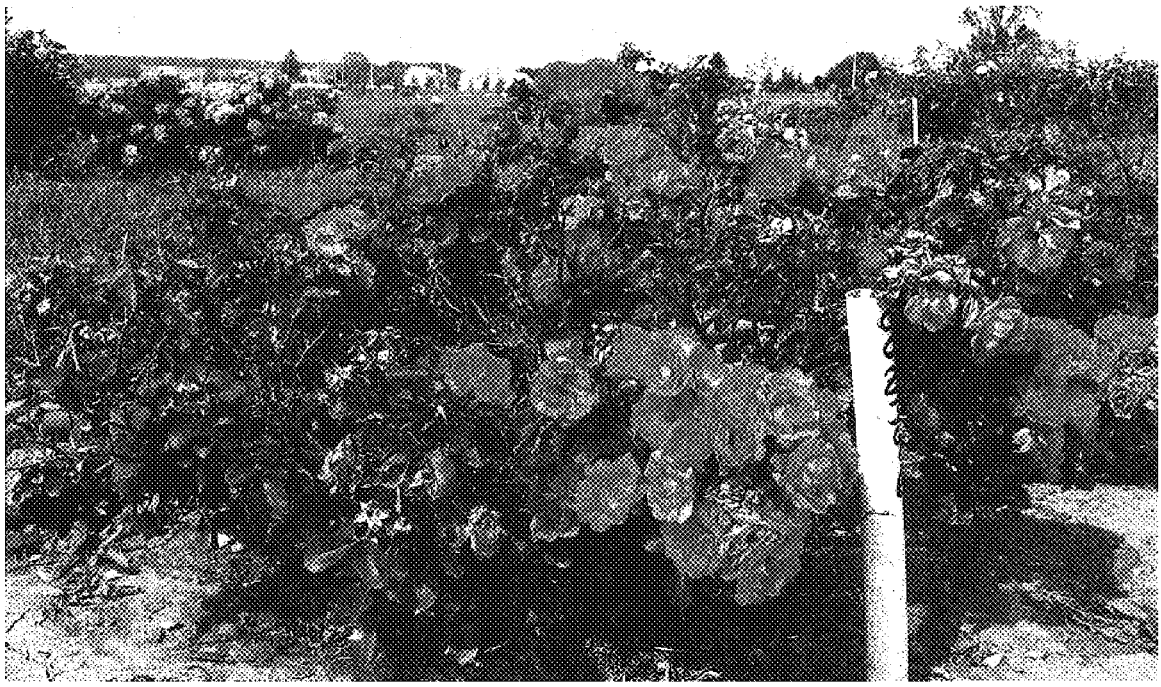
FIG. 1 shows the typical flowering specimen of the new variety wherein the compact spreading ground cover growth habit is illustrated.
Figure 2:
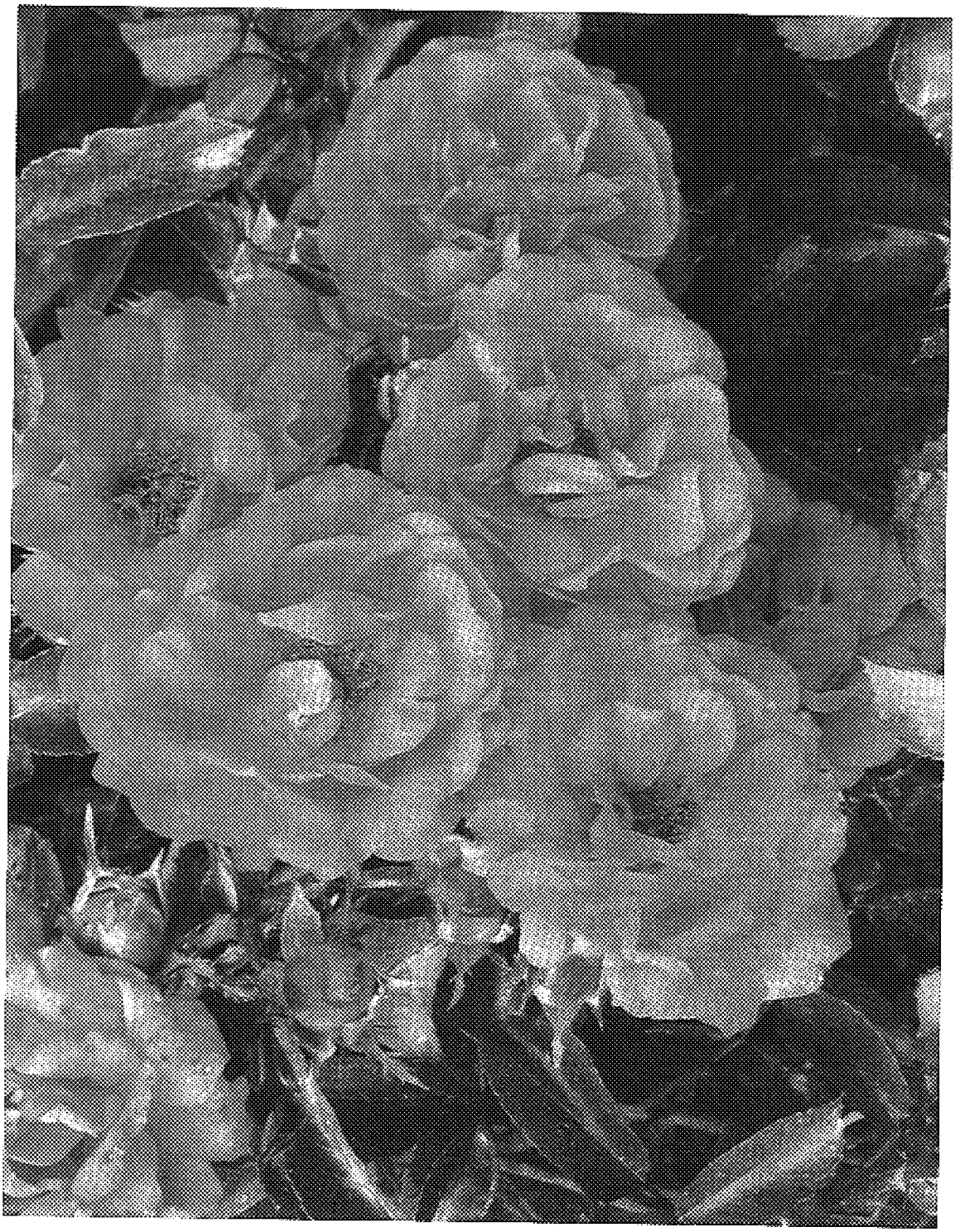
FIG. 2 shows a close view of the attractive deep-coral-orange blossoms and buds, as well as the foliage of the new variety.

The chart used in the identification of colors is that of The Royal Horticultural Society (R.H.S. Colour Chart), London, England. The description is based on the observation of three-year-old specimens of the new variety during June 2006 while growing outdoors on 'Dr. Huey' rootstock near West Grove, Pa., U.S.A.

Class: Landscape Shrub.

Plant:

*Height.*—Approximately 25 to 35 cm on average at the end of the growing season.

*Width.*—Approximately 55 to 65 cm on average at the end of the growing season.

*Habit.*—Low rounded mound.

Branches:

*Color.*—Young stems: Yellow-Green Group 144C with some highlights of Red Group 53C. Adult wood: Yellow-Green Group 144A.

*Thorns.*—Size: approximately 1 cm in length from base to point on average. Configuration: commonly sharply pointed with the tip nearly perpendicular to the stem and pointing upward. Quantity: typically approximately 5 or 6 over a stem length of 10 cm. Color: near Yellow-Green Group 151A on young stems and near Brown Group 200D on mature wood and more glaucous.

Leaves:

*Length.*—Varies widely with number of leaflets, for a mature five-leaflet leaf approximately 7 to 8 cm including the petiole on average, and for a mature seven-leaflet leaf approximately 9 to 10 cm including the petiole on average.

*Width.*—For a five-leaflet leaf approximately 5 to 5.5 cm on average at the widest point, and for a seven-leaflet leaf approximately 7 to 7.5 cm on average at the widest point.

*Leaflets.*—Number: 3 (rarely), 5 (more commonly), 7 (more typically), and 9 (rarely). Arrangement: alternate and pinnate. Shape: typically elliptical to broadly elliptical, with typically a shortly attenuate base, and typically with a broadly acute to rounded tip. Margins: serrulate. Texture: glabrous on the upper and under surfaces and papyraceous. Overall appearance: small, dense, medium-green in coloration, and glossy. Color (young foliage): Upper surface; near Green Group 137C. Under surface: near Green Group 138C with some darkening to Green Group 137C. Color (adult foliage): Upper surface: near Green Group 137C. Under surface: near Green Group 138C with some lightening to Green Group 137C.

*Petioles.*—Length: approximately 23 mm on average. Diameter: approximately 1.4 mm on average. Color: Yellow-Green Group 144C.

*Stipules.*—Length: approximately 9 mm on average. Width: approximately 7 mm on average. Color: near Yellow-Green Group 144C towards the middle, and near Green Group 137A at the edges.

Inflorescence:

*Number of flowers.*—Commonly 12 to 14 per stem in a cluster.

*Peduncle.*—Approximately 15 to 20 mm in length on average, and approximately 1.5 to 2 mm in diameter on average.

*Sepals.*—Typically five in number, approximately 14 to 20 mm in length on average, approximately 6 mm in width on average, near Green Group 143A on the inner and outer surfaces, and with a few generally lanceolate-shaped foliaceous extensions at the edges which commonly are approximately 7 to 11 mm in length and approximately 2.5 to 4.5 mm in width.

*Buds.*—Shape: Ovoid. Size: very small, and approximately 8 to 10 mm in length and approximately 6 mm in width on average as the calyx breaks. Color: as the bud cracks the petals are Yellow Group 13C on the upper and under surfaces.

*Flower.*—Form: Double. Shape: cup-like when fully open. Diameter: approximately 4 to 4.5 cm on average when fully open. Color at bud cracking: Upper surface: Red Group 42A at the apex, and Yellow Group 3D at the base. Under surface: primarily Red Group 43D at the apex and Yellow Group 3D at the base. Color newly opened: Upper surface: Red Group 42A at the apex, and Yellow Group 3D at the base. Under surface: primarily Red Group 43D at the apex and Yellow Group 3D at the base. Color fully opened: Upper surface: Red Group 39A with a small amount of Yellow Group 11C at the base. Under surface: primarily Red Group 39C with some Yellow Group 11D at the base. Color stability: there is a slight change in coloration from the time of first opening to petal drop. Fragrance: relatively mild spice. Petal shape: obovate to narrowly obovate to narrowly obcordate. Petal number: commonly approximately 50 to 55 on average under normal growing conditions. Petaloids: commonly 1 to 5 per blossom, irregularly shaped, approximately 20 mm in length, and approximately 8 mm in width. Petal texture: glabrous, membranaceus, relatively thin, and semi-transparent. Petal margin: entire, and tends to be slightly revolate. Petal apex: obtuse. Petal base: narrowly cuneate. Petal size: commonly approximately 2 to 2.5 cm in length on average, and approximately 1.5 to 2 cm in width on average. Petal drop: very good with the petals detaching cleanly and freely before drying. Stamen number: approximately 30 to 35 on average. Filaments: typically approximately 6 mm in length, and approximately 1 mm in diameter. Pollen: present and near Yellow-Orange Group 22A in coloration. Pistils: approximately 30 on average. Styles: approximately 6 mm in length on average, and less than 1 mm in width on average. Receptacle: slightly glaucous, commonly approximately 2.5 to 2.8 mm in size when the flower is completely open, and near Green Group 138A in coloration. Hips: none observed. Lasting quality: commonly approximately 7 to 8 days on the plant, and approximately 5 to 6 days when cut and placed in a vase.

Development:

*Vegetation.*—Vigorous and procumbent thin branches with upright thin shoots and a generally restrained growth.

*Blossoming.*—Abundant and nearly continuous.

*Resistance to diseases.*—Excellent with respect to Black Spot, Powdery Mildew, and Rust.

*Formation of hips/seeds.*—Sparsely formed.

*Hardiness.*—Proven hardy in U.S.D.A. Hardiness Zone No. 5.

*Heat tolerance.*—Testing is underway.

I claim:

1. A new and distinct Shrub Rose plant characterized by the following combination of characteristics:

(a) abundantly forms in clusters on a nearly continuous basis attractive double cup-like deep-coral-orange blossoms that self clean well, (b) exhibits a spreading ground cover growth habit, (c) forms glossy medium-green foliage that contrasts well with the blossom coloration, (d) develops well following asexual reproduction, (e) is highly resistant to Black Spot, Powdery Mildew, and Rust; and (f) is particularly well suited for providing attractive ornamentation as a mass planting and when grown in containers;

substantially as herein shown and described.

* * * * *